(12) United States Patent
Okamoto

(10) Patent No.: US 10,117,567 B2
(45) Date of Patent: Nov. 6, 2018

(54) ENDOSCOPE

(71) Applicant: OLYMPUS CORPORATION, Tokyo (JP)

(72) Inventor: Yasuhiro Okamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/252,767

(22) Filed: Aug. 31, 2016

(65) Prior Publication Data

US 2016/0367111 A1 Dec. 22, 2016

Related U.S. Application Data

(63) Continuation of application No. PCT/JP2015/058039, filed on Mar. 18, 2015.

(30) Foreign Application Priority Data

Sep. 26, 2014 (JP) .................................. 2014-196842

(51) Int. Cl.
*A61B 1/00* (2006.01)
*A61B 1/005* (2006.01)

(52) U.S. Cl.
CPC .............. *A61B 1/0052* (2013.01); *A61B 1/00* (2013.01); *A61B 1/0057* (2013.01)

(58) Field of Classification Search
CPC . A61B 1/00064; A61B 1/00066; A61B 1/005; A61B 1/0051; A61B 1/0052;
(Continued)

(56) References Cited

U.S. PATENT DOCUMENTS

2008/0139886 A1 6/2008 Tatsuyama
2013/0190566 A1* 7/2013 Miyoshi ............... A61B 1/0057
600/131

FOREIGN PATENT DOCUMENTS

CN 103582444 A 2/2014
EP 2 649 922 A1 10/2013
(Continued)

OTHER PUBLICATIONS

Extended Supplementary European Search Report dated Nov. 7, 2017 in European Patent Application No. 15 84 3376.3.
(Continued)

*Primary Examiner* — John P Leubecker
*Assistant Examiner* — Pamela F Wu
(74) *Attorney, Agent, or Firm* — Scully, Scott, Murphy & Presser, P.C.

(57) ABSTRACT

An endoscope includes a bending section being disposed in an insertion section, a plurality of towing members disposed in the insertion section and in an operation section from the bending section, a disk member turnably provided in the operation section and configured to turn to tow and loosen the plurality of towing members, the plurality of towing members being suspended in an outer circumference of the disk member, operation members turnably disposed in the operation section and configured to turn the disk member to bend the bending section, and a turning shaft configured to turnably axially support the disk member and the operation members with respect to the operation section in a position decentered to the distal end side by a predetermined distance d with respect to a center of the disk member in an initial state in which the bending section is linear.

3 Claims, 12 Drawing Sheets

(58) Field of Classification Search
CPC ... A61B 1/0053; A61B 1/0055; A61B 1/0056; A61B 1/0057; A61B 1/0058; A61B 1/008; A61B 2017/003; A61B 2017/00318; A61B 2017/00323; A61B 2017/00327; A61B 2017/00331; A61M 25/0147
USPC .......................................................... 600/146
See application file for complete search history.

(56) References Cited

FOREIGN PATENT DOCUMENTS

| JP | 2002-165753 A | 6/2002 |
| JP | 2007-061218 A | 3/2007 |
| JP | 2008-142199 A | 6/2008 |

OTHER PUBLICATIONS

International Search Report dated Jun. 9, 2015 issued in corresponding International Patent Application No. PCT/JP2015/058039.

* cited by examiner

US 10,117,567 B2

ENDOSCOPE

CROSS REFERENCE TO RELATED APPLICATION

This application is a continuation application of PCT/JP2015/058039 filed on Mar. 18, 2015 and claims benefit of Japanese Application No. 2014-196842 filed in Japan on Sep. 26, 2014, the entire contents of which are incorporated herein by this reference.

BACKGROUND OF THE INVENTION

1. Field of the Invention

The present invention relates to an endoscope in which a bending operation knob for bending a bending section of an insertion section is provided in an operation section.

2. Description of the Related Art

An endoscope including an insertion section insertable into a subject for observing a subject that an observer cannot directly view has been used. As the endoscope, there is an endoscope in which a bending section bent by hand operation is provided in order to improve insertability of the insertion section. The bending section of the endoscope is bent in an up-down direction or a left-right direction by a bending operation knob provided in an operation section.

Such an endoscope is disclosed in, for example, Japanese Patent Application Laid-Open Publication No. 2008-142199. A pulley that winds an operation wire and tows and loosens the operation wire according to turning operation of the bending operation knob is provided. Positions of a center of the pulley and a turning center are shifted to prevent slack from occurring in the operation wire when the bending section is operated and make it possible to obtain satisfactory feeling in operation.

SUMMARY OF THE INVENTION

An endoscope according to an aspect of the present invention includes: an operation section provided on a hand side, which is a proximal end side; an insertion section extending to a distal end side from the operation section, a bending section being disposed in the insertion section; a plurality of towing members disposed in the insertion section and in the operation section from the bending section; a disk member turnably provided in the operation section and configured to turn to tow and loosen the plurality of towing members, the plurality of towing members being suspended in an outer circumference of the disk member; an operation member turnably disposed in the operation section and configured to turn the disk member to bend the bending section; and a turning shaft configured to turnably axially support the disk member and the operation member with respect to the operation section in a position decentered to the distal end side by a predetermined distance with respect to a center of the disk member in an initial state in which the bending section is linear.

DETAILED DESCRIPTION OF THE
PREFERRED EMBODIMENT(S)

The present invention is explained below with reference to the drawings. Note that, in the respective figures referred to in the following explanation, scales are differentiated for each of components in order to show the respective components in sizes recognizable on the drawings. The present invention is not limited to only numbers of components, shapes of the components, ratios of sizes of the components, and relative positional relations of the respective components described in the figures.

First Embodiment

Figure 1:
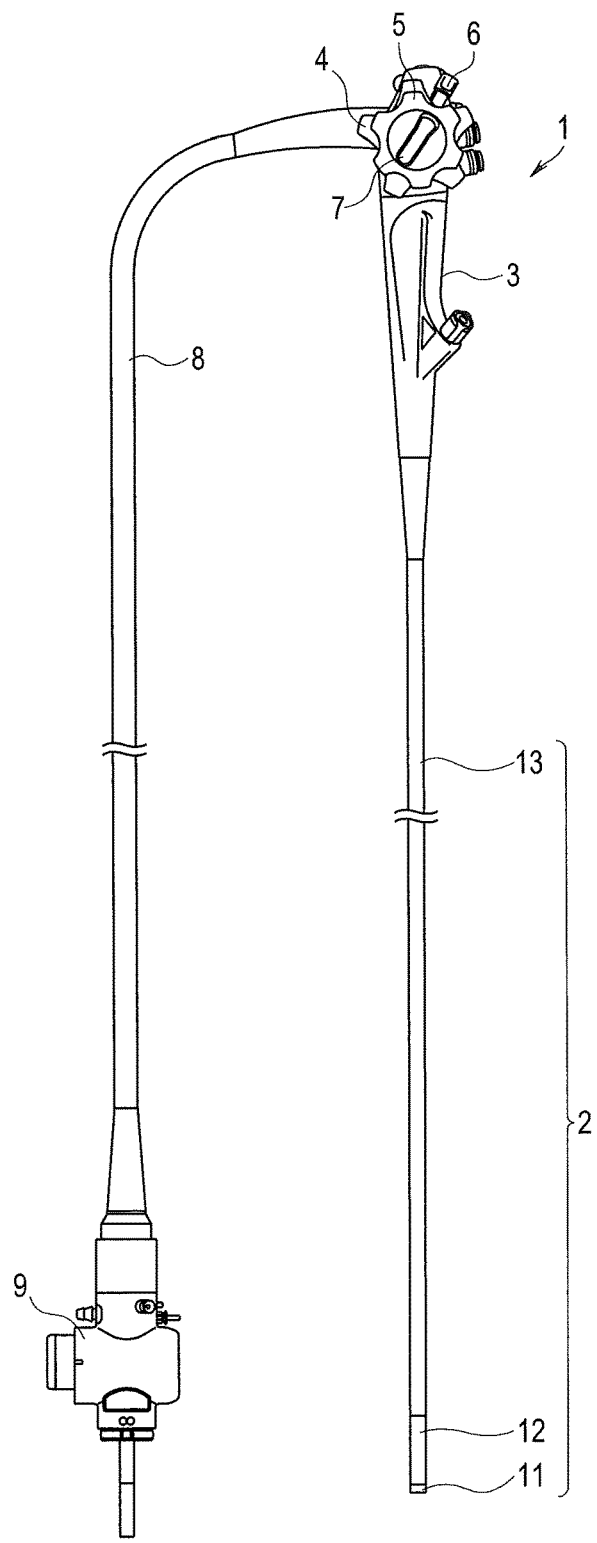
FIG. 1 is a diagram showing an overall configuration of an endoscope in a first embodiment of the present invention.
Figure 2:
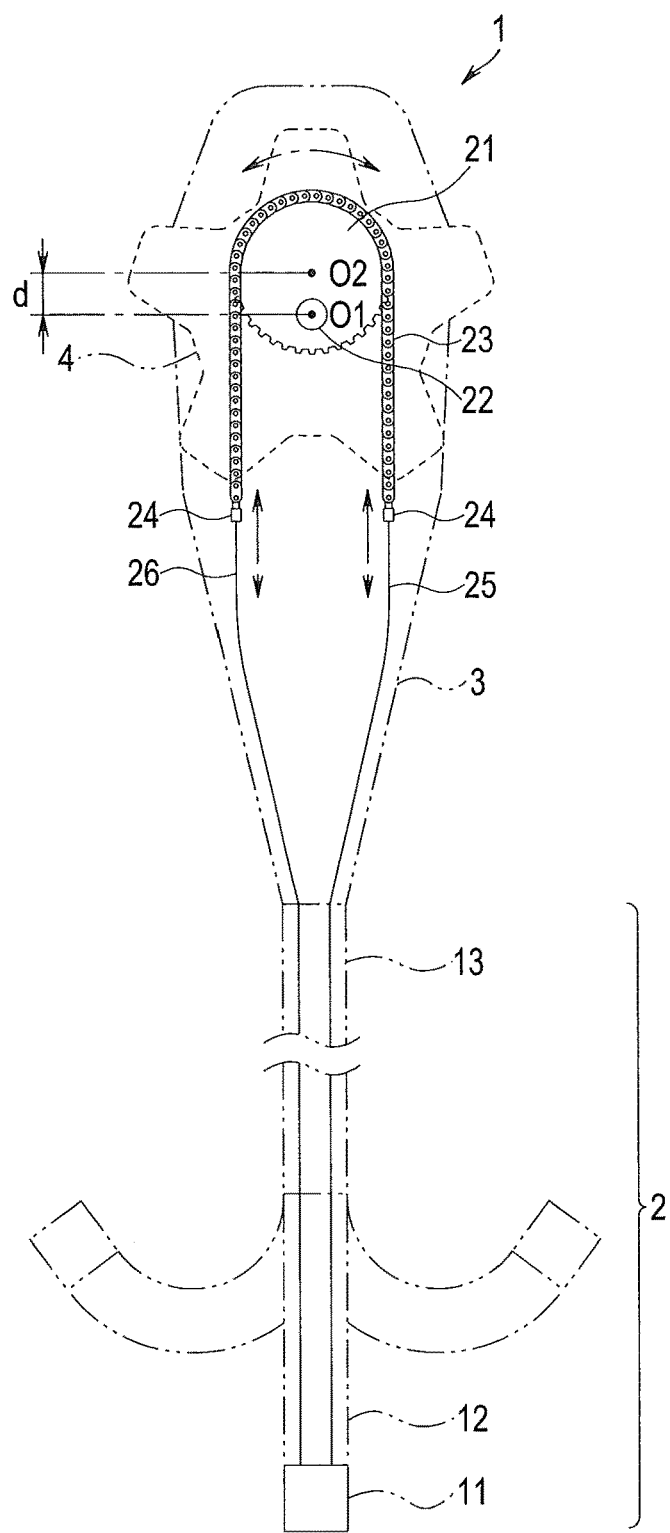
FIG. 2 is a schematic diagram of the endoscope showing a configuration in which a bending section is bent by a turning mechanism that turns in association with a bending operation knob in the first embodiment of the present invention.
Figure 3:
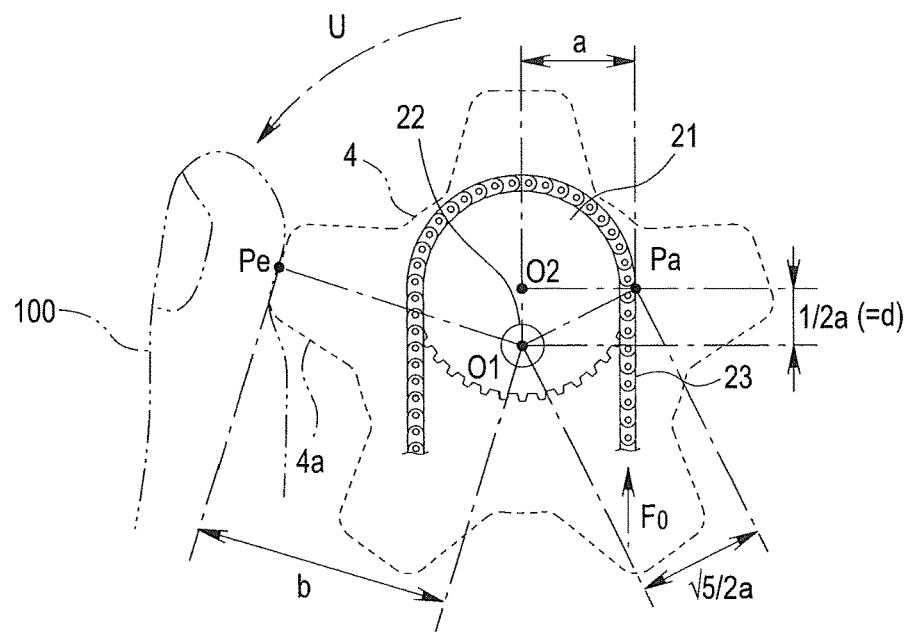
FIG. 3 is a schematic diagram showing a turning position of the bending operation knob at a time when the bending section is bent upward from an initial state in the first embodiment of the present invention.
Figure 4:
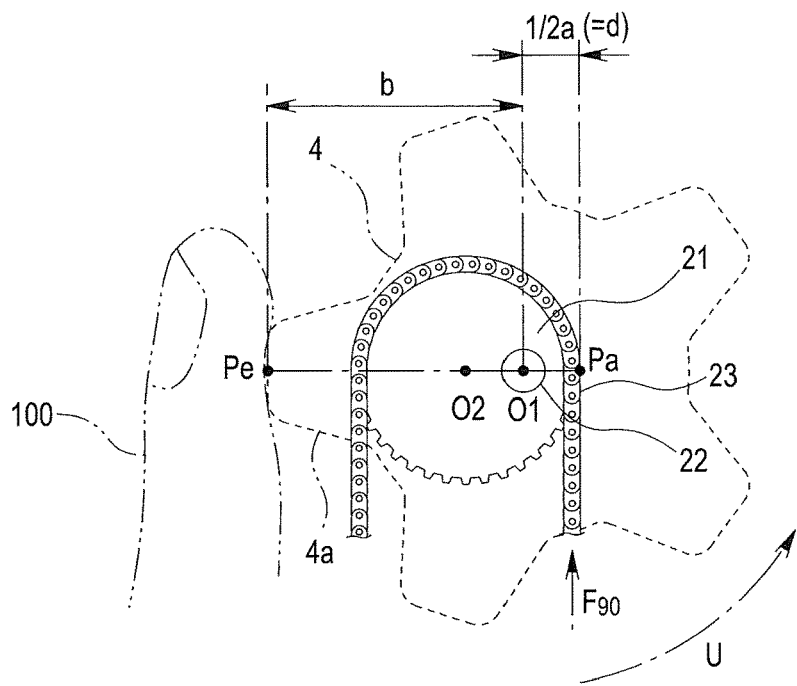
FIG. 4 is a schematic diagram showing a turning position of the bending operation knob at a time when the bending section is bent 90 degrees upward in the first embodiment of the present invention.
Figure 5:
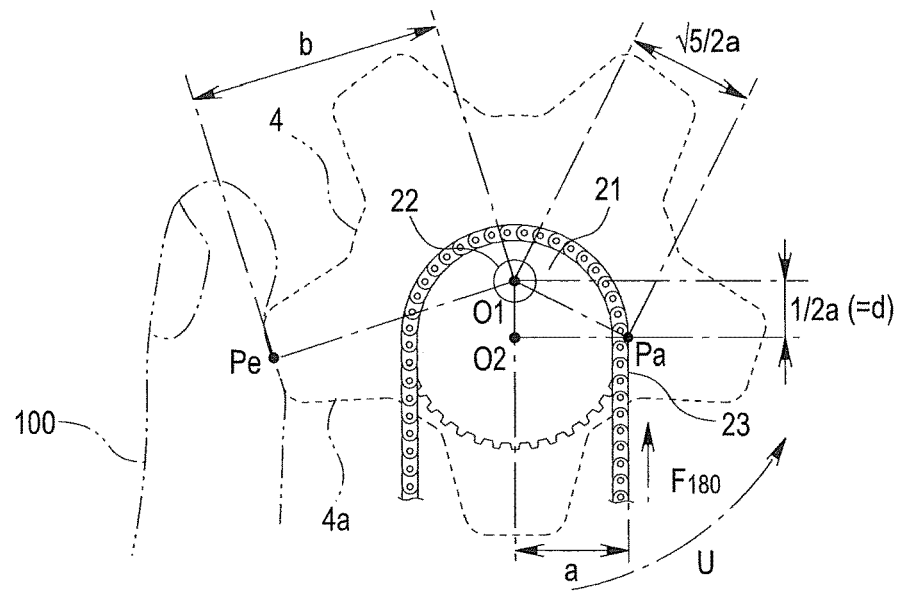
FIG. 5 is a schematic diagram showing a turning position of the bending operation knob at a time when the bending section is bent 180 degrees upward in the first embodiment of the present invention.
Figure 6:
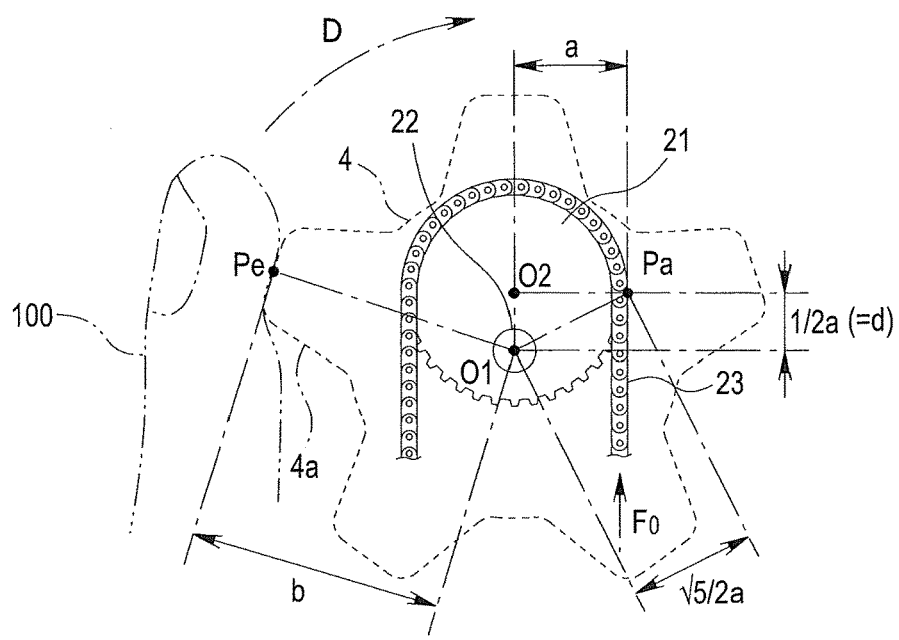
FIG. 6 is a schematic diagram showing a turning position of the bending operation knob at a time when the bending section is bent downward from the initial position in the first embodiment of the present invention.
Figure 7:
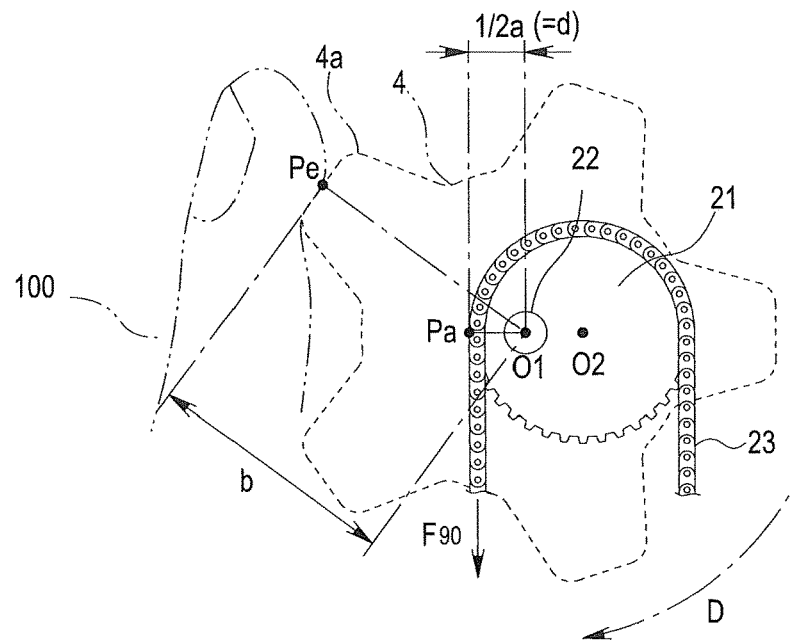
FIG. 7 is a schematic diagram showing a turning position of the bending operation knob at a time when the bending section is bent 90 degrees downward in the first embodiment of the present invention.
Figure 8:
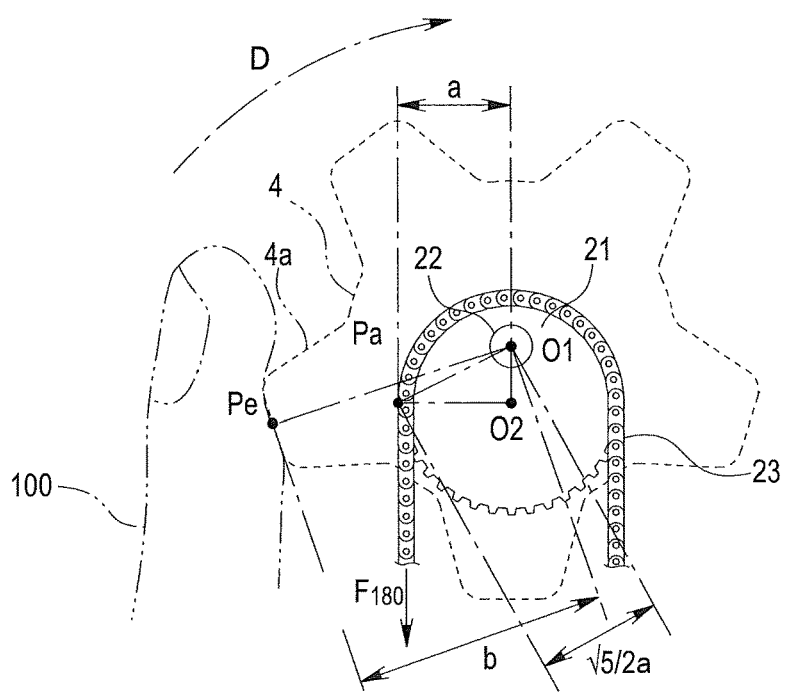
FIG. 8 is a schematic diagram showing a turning position of the bending operation knob at a time when the bending section is bent 180 degrees downward in the first embodiment of the present invention.
Figure 9:
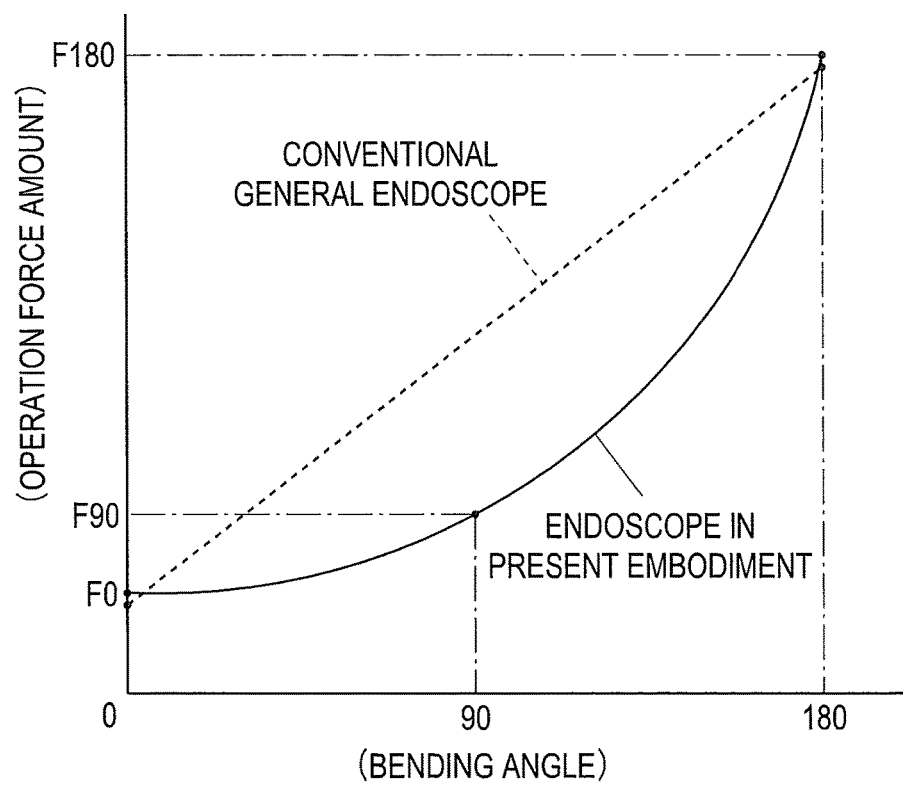
FIG. 9 is a graph showing a change in an operation force amount of the bending operation knob with respect to a bending angle of the bending section in the first embodiment of the present invention.

FIG. 1 to FIG. 9 relate to a first embodiment of the present invention. FIG. 1 is a diagram showing an overall configuration of an endoscope. FIG. 2 is a schematic diagram of the endoscope showing a configuration in which a bending section is bent by a turning mechanism that turns in association with a bending operation knob. FIG. 3 is a schematic diagram showing a turning position of the bending operation knob at a time when the bending section is bent upward from an initial state. FIG. 4 is a schematic diagram showing a turning position of the bending operation knob at a time when the bending section is bent 90 degrees upward. FIG. 5 is a schematic diagram showing a turning position of the bending operation knob at a time when the bending section is bent 180 degrees upward. FIG. 6 is a schematic diagram showing a turning position of the bending operation knob at a time when the bending section is bent downward from the initial position. FIG. 7 is a schematic diagram showing a turning position of the bending operation knob at a time when the bending section is bent 90 degrees downward. FIG. 8 is a schematic diagram showing a turning position of the bending operation knob at a time when the bending section is bent 180 degrees downward. FIG. 9 is a graph showing a change in an operation force amount of the bending operation knob with respect to a bending angle of the bending section.

As shown in FIG. 1, an endoscope 1 configured to include an insertion section 2 inserted into a subject, an operation section 3 consecutively connected to a hand side, which is a proximal end side of the insertion section 2, a universal cord 8 extended from the operation section 3, and a connector 9 provided at an extending end of the universal cord 8. Note that the endoscope 1 is electrically connected to not-shown external apparatuses such as a video processor and a light source apparatus via the connector 9.

In the operation section 3, an up-down bending operation knob 4 functioning as an operation member that is turned to bend a bending section 12 of the insertion section 2 in an up-down direction and a left-right bending operation knob 5 functioning as an operation member that is turned to bend the bending section 12 to a left-right direction are provided.

The up-down bending operation knob 4 and the left-right bending operation knob 5 are disk-like members in which five protrusion sections (4a) for finger hook are radially provided from a center (a turning center).

Further, in the operation section 3, a fixing lever 6 that fixes a turning position of the up-down bending operation knob 4 and a fixing knob 7 that fixes a turning position of the left-right bending operation knob 5 are provided.

In the insertion section 2, a distal end portion 11, the bending section 12, and a flexible tube section 13 are jointly provided in order from a distal end side. The insertion section 2 is formed thin and long to be easily inserted into a subject.

The bending section 12 is bent in, for example, upward, downward, left, and right four directions by turning operation of the up-down bending operation knob 4 and the left-right bending operation knob 5 to thereby change an observation direction of an image pickup unit 30 explained below provided in the distal end portion 11 and improve insertability of the distal end portion 11 in the subject.

In the endoscope 1, as shown in FIG. 2, a sprocket 21 functioning as a disk member, which is a chain wheel, connected via a turning shaft 22 coupled to a center (a turning center) O1 of the up-down bending operation knob 4 to axially support the up-down bending operation knob 4 is disposed in the operation section 3. Note that the disk member may be a pulley rather than the sprocket 21.

The sprocket 21 is axially supported by the turning shaft 22 such that, when the bending section 12 is linear, a center O2 is decentered in a predetermined direction, in the figure, an upward side of the operation section 3 at a predetermined distance d from the turning center O1 of the up-down bending operation knob 4.

In other words, in the sprocket 21, the turning center O1 is decentered by the predetermined distance d to the distal end side along a longitudinal direction of the operation section 3 with respect to the center O2.

Note that the center (the turning center) O1 of the turning shaft 22 and the up-down bending operation knob 4 and the center O2 of the sprocket 21 are juxtaposed along a center axis of the insertion section 2 when the bending section 12 is in a neutral linear state (a neutral initial state).

Only an upper semicircular portion of a chain 23, which is a part of a towing member, is suspended and meshed with the sprocket 21. A pair of operation wires 25, which is a part of the towing member, is connected to both end portions of the chain 23 via connecting members 24.

The operation wires 25 are disposed to be inserted through the insertion section 2 from the operation section 3. Distal ends of the operation wires 25 are connected to a most-distal-end bending piece provided at a not-shown distal end in the bending section 12.

A not-shown plurality of bending pieces are turnably coupled on an inside of the bending section 12. When the operation wires 25 are towed and loosened according to turning of the up-down bending operation knob 4, the bending section 12 is configured to bend in the up-down direction.

Note that, although not shown in the figure, in the operation section 3, as in the up-down bending operation knob 4, the sprocket 21, the chain 23, the operation wires 25, and the like corresponding to the left-right bending operation knob 5 are provided. Therefore, when the operation wires 25 are towed and loosened according to the turning of the left-right bending operation knob 5, the bending section 12 is configured to bend in the left-right direction. Such a bending structure in which the plurality of bending pieces are provided in the bending section 12 is well known. Therefore, explanation of the bending structure is omitted.

A relation between rotation angles and operation force amounts of the respective bending operation knobs 4 and 5 in the endoscope 1 configured as explained above is explained in detail below with reference to the drawings.

Note that, for convenience of explanation, a bending angle of the bending section 12 is set to an angle same as a rotation angle of the respective bending operation knobs 4 and 5.

Further, in the following explanation, a relation between a rotation angle and an operation force amount of the up-down bending operation knob 4 is illustrated. A relation between a rotation angle and an operation force amount of the left-right bending operation knob 5 is the same as the relation of the rotation angle and operation force amount of the up-down bending operation knob 4. Therefore, explanation concerning the left-right bending operation knob 5 is omitted without illustrating the relation.

In the endoscope 1, as shown in FIG. 3 to FIG. 8, the center O2 of the sprocket 21 is decentered on an upward side along a longitudinal direction of the operation section 3 while having a predetermined distance d (d=½a), which is a half ½a of a radius a of the sprocket 21, with respect to the center (the turning center) O1 of the up-down bending operation knob 4 provided in the operation section 3, that is, the center (the turning center) O1 of the turning shaft 22.

That is, in the sprocket 21, the turning center O1 is decentered with respect to the center O2 by a predetermined distance ½a (=d) to the distal end side along the longitudinal direction of the operation section 3.

Note that, in the following explanation, a point where a finger (a thumb) F of a user is hooked to the protrusion sections 4a of the up-down bending operation knob 4 is represented as an action point Pe, a distance from the action point Pe to the turning center O1 is represented as a predetermined distance b, and a point on an extended line in a lateral direction (a horizontal direction) of the center O2 of the sprocket 21 is represented as a power point Pa.

First, a relation between a rotation angle of the up-down bending operation knob 4 and a turning force amount of the operation knob at a time when the bending section 12 bends in an upward direction is explained below with reference to FIG. 3 to FIG. 5.

When a bending angle of the bending section 12 to be bent to an upward side is changed from 0 (zero) degrees in an initial state of the bending angle, in which the bending section 12 is linear, shown in FIG. 3 to 90 degrees, as shown in FIG. 4, the up-down bending operation knob 4 is turned 90 degrees around the turning center O1 in a counterclockwise direction.

In this state, an operation force amount necessary for an operation force amount $F_0$, which is a towing force of the operation wires 25 for bending the bending section 12 at a time when the bending section 12 is further bent to the upward side from the bending angle of 0 degrees, is the following Equation (1) from a relation between a distance $\sqrt{5}/2 \cdot a$ from the turning center O1 to the power point Pa and the distance b from the turning center O1 to the action point Pe.

$$\text{Operation force amount } F0 = F_0 \cdot \sqrt{5}/2 \cdot a/b \tag{1}$$

Note that the distance from the turning center O1 to the power point Pa can be calculated by a Pythagorean Theorem.

When the bending section 12 is further bent to the upward side from the state of the bending angle of 90 degrees shown in FIG. 4 to change the bending angle of the bending section 12 to 180 degrees, as shown in FIG. 5, the up-down bending operation knob 4 is turned 90 degrees around the turning center O1 in the counterclockwise direction. At this point, the sprocket 21 turns 90 degrees around the turning center O1 to approach a finger 100 of the user.

That is, when the bending angle of the bending section 12 is changed to 180 degrees to the upward side from the state of the bending angle of 0 (zero) degrees of the bending section 12 shown in FIG. 3, the up-down bending operation knob 4 is turned 180 degrees around the turning center O1 counterclockwise.

In this state, an operation force amount F90 necessary for a bending force amount $F_{90}$ for bending the bending section 12 at a time when the bending section 12 is further bent upward from the bending angle of 90 degrees is the following Equation (2) from a relation between a distance ½·a from the turning center O1 to the power point Pa and the distance b from the turning center O1 to the action point Pe.

$$\text{Operation force amount } F90 = F_{90} \cdot 1/2 \cdot a/b \tag{2}$$

Note that an operation force amount F180 necessary for a bending force amount $F_{180}$ at a time when the bending angle of the bending section 12 is changed to 180 degrees shown in FIG. 5 is the following Equation (3) from the relation between the distance $\sqrt{5}/2 \cdot a$ from the turning center O1 to the power point Pa and the distance b from the turning center O1 to the action point Pe.

$$\text{Operation force amount } F180 = F_{180} \cdot \sqrt{5}/2 \cdot a/b \tag{3}$$

A relation between a rotation angle and an operation force amount of the up-down bending operation knob 4 at a time when the bending section 12 bends in a downward direction is explained below with reference to FIG. 6 to FIG. 8.

When a bending angle of the bending section 12 to be bent to a downward side is changed from 0 (zero) degrees in the initial state of the bending angle, in which the bending section 12 is linear, shown in FIG. 6 to 90 degrees (−90 degrees), as shown in FIG. 7, the up-down bending operation knob 4 is turned 90 degrees (−90 degrees) around the turning center O1 in the counterclockwise direction.

In this state, an operation force amount F0 necessary for an operation force amount $F_0$, which is a towing force of the operation wires 25 for bending the bending section 12 at a time when the bending section 12 is further bent to the downward side from the bending angle of 0 degrees, is the following Equation (4) from the relation between the distance $\sqrt{5}/2 \cdot a$ from the turning center O1 to the power point Pa and the distance b from the turning center O1 to the action point Pe.

$$\text{Operation force amount } F0 = F_0 \cdot \sqrt{5}/2 \cdot a/b \tag{4}$$

When the bending section 12 is further bent to the downward side from the state of the bending angle of 90 degrees (−90 degrees) shown in FIG. 7 to change the bending angle of the bending section 12 to 180 degrees (−180 degrees), as shown in FIG. 8, the up-down bending operation knob 4 is further turned 90 degrees (−90 degrees) around the turning center O1 in the counterclockwise direction. At this point, the sprocket 21 turns 90 degrees (−90 degrees) around the turning center O1 to move away from the finger 100 of the user.

That is, when the bending angle of the bending section 12 is changed to 180 degrees (−180 degrees) to the downward side from the state of the bending angle of 0 (zero) degrees of the bending section 12 shown in FIG. 6, the up-down bending operation knob 4 is turned 180 degrees (−180 degrees) around the turning center O1 counterclockwise.

In this state, an operation force amount F90 (F-90) necessary for the bending force amount $F_{90}$ for bending the bending section 12 at a time when the bending section 12 is further bent downward from the bending angle of 90 degrees (−90 degrees) is the following Equation (5) from a relation between the distance a from the turning center O1 to the power point Pa and the distance b from the turning center O1 to the action point Pe.

$$\text{Operation force amount } F90 = F_{90} \cdot 1/2 \cdot a/b \qquad (5)$$

Note that an operation force amount F180 (F-180) necessary for the bending force amount $F_{180}$ at a time when the bending angle of the bending section 12 is changed to 180 degrees (−180 degrees) shown in FIG. 8 is the following Equation (6) from the relation between the distance $\sqrt{5}/2 \cdot a$ from the turning center O1 to the power point Pa and the distance b from the turning center O1 to the action point Pe.

$$\text{Operation force amount } F180 = F_{180} \cdot \sqrt{5}/2 \cdot a/b \qquad (6)$$

On the other hand, in a general endoscope, the center O1 of the up-down bending operation knob 4 and the center O2 of the sprocket 21 coincide with each other and are not decentered. Therefore, the relation between the distance a from the turning center O1 to the power point Pa and the distance b from the turning center O1 to the action point Pe is invariable.

Therefore, the operation force amount F0 necessary for the operation force amount $F_0$, which is a towing force of the operation wires 25 for bending the bending section 12 at a time when the bending section 12 is further bent to the upward/downward sides from the bending angle of 0 degrees, in the conventional endoscope is the following Equation (7) from the relation between the distance a from the turning center O1 to the power point Pa and the distance b from the turning center O1 to the action point Pe in both the upward and downward directions.

$$\text{Operation force amount } F0 = F_0 \cdot a/b \qquad (7)$$

The operation force amount F90 (F-90) necessary for the bending force amount $F_{90}$ for bending the bending section 12 at a time when the bending section 12 is further bent upward/downward from the bending angle of 90 degrees (−90 degrees) in the conventional endoscope is the following Equation (8) because the distance a from the turning center O1 to the power point Pa and the distance b from the turning center O1 to the action point Pe do not change in both the upward and downward directions.

$$\text{Operation force amount } F90(F\text{-}90) = F_{90} \cdot a/b \qquad (8)$$

Further, the operation force amount F180 (F-180) necessary for the bending force amount $F_{180}$ at a time when the bending angle of the bending section 12 is changed to 180 degrees (−180 degrees) in the conventional endoscope is, from the relationship, the following Equation (9) because the distance a from the turning center O1 to the power point Pa and the distance b from the turning center O1 to the action point Pe do not change in both the upward and downward directions.

$$\text{Operation force amount } F180(F\text{-}180) = F_{180} \cdot a/b \qquad (9)$$

A table summarizing the above is shown below.

TABLE 1

Transition of an operation force amount of the bending operation knob

| | Bending angle of the bending section (Rotation angle of the bending operation knob) and operation force amount | | |
|---|---|---|---|
| | 0°/F0 | 90°/F90 | 180°/F180 |
| Decentering is absent (general endoscope) | $F_0 \cdot a/b$ | $F_{90} \cdot a/b$ | $F_{180} \cdot a/b$ |
| Decentering is present in an UP direction | $F_0 \cdot \sqrt{5}/2 \cdot a/b$ | $F_{90} \cdot 1/2 \cdot a/b$ | $F_{180} \cdot \sqrt{5}/2 \cdot a/b$ |
| Decentering is present in a DOWN direction | $F_0 \cdot \sqrt{5}/2 \cdot a/b$ | $F_{90} \cdot 1/2 \cdot a/b$ | $F_{180} \cdot \sqrt{5}/2 \cdot a/b$ |

In the endoscope 1, when the distance a from the turning center O1 to the power point Pa is a half (b=2a) of the distance b from the turning center O1 to the action point Pe, the respective equations (1) to (6) are calculated as follows.

$$F0 = F_0 \cdot \sqrt{5}/2 \cdot a/(2 \cdot a) = F_0 \cdot \sqrt{5}/4 \qquad (1), (4)$$

$$F90(F\text{-}90) = F_{90} \cdot a \cdot 1/2 / 2 \cdot a = F_{90} \cdot 1/4 \qquad (2), (5)$$

$$F180(F\text{-}180) = F_{180} \cdot a \cdot 1/2 \cdot a = F_{180} \sqrt{5}/4 \qquad (3), (6)$$

Note that, in the conventional endoscope, when the distance a from the turning center O1 to the power point Pa is a half (b=2a) of the distance b from the turning center O1 to the action point Pe, the respective equations (7) to (9) are calculated as follows.

$$F0 = F_0 \cdot a/2 \cdot a = F_0 \cdot 1/2 \qquad (7)$$

$$F90(F\text{-}90) = F_{90} \cdot a/2 \cdot a = F_{90} \cdot 1/2 \qquad (8)$$

$$F180(F\text{-}180) = F_{180} \cdot a/2 \cdot a = F_{180} \cdot 1/2 \qquad (9)$$

A table summarizing the above is shown below.

TABLE 2

Transition of an operation force amount of the bending operation knob (b = 2a)

| | Bending angle of the bending section (Rotation angle of the bending operation knob) and operation force amount | | |
|---|---|---|---|
| | 0°/F0 | 90°/F90 | 180°/F180 |
| Decentering is absent (general endoscope) | $F_0 \cdot 1/2$ | $F_{90} \cdot 1/2$ | $F_{180} \cdot 1/2$ |
| Decentering is present in an UP direction | $F_0 \cdot \sqrt{5}/4$ | $F_{90} \cdot 1/4$ | $F_{180} \cdot \sqrt{5}/4$ |
| Decentering is present in a DOWN direction | $F_0 \cdot \sqrt{5}/4$ | $F_{90} \cdot 1/4$ | $F_{180} \cdot \sqrt{5}/4$ |

The above is the explanation of the operation force amount of the up-down bending operation knob 4 with respect to the bending angle for bending the bending section 12. The same applies to the left-right bending operation knob 5. Therefore, explanation is omitted concerning the left-right bending operation knob 5.

In the endoscope 1 in the present embodiment, as shown in a graph of FIG. 9, when compared with a linear change indicated by a broken line in the figure due to an operation force amount of a conventional (existing) general endoscope, the operation force amount F0 in an initial motion from the bending angle of 0 degrees at a time when the bending section 12 is bent and the operation force amount F180 (F-180) at the bending angle of 180 degrees (−180 degrees) are approximately 1.12 $\{=(F_0\cdot\sqrt{5}/2)/(F_0\cdot 1/2)\}$ times. The operation force amounts slightly increase.

However, in the endoscope 1, the operation force amount F90 (F-90) for bending the bending section 12 to the bending angle of 90 degrees (−90 degrees) only has to be a force amount of a half $\frac{1}{2}\{=(F_{90}\cdot 1/4)/(F_{90}\cdot 1/2)\}$. An operation force amount at the time when the bending section 12 is bent from the bending angle of 0 degrees to the bending angle of 180 degrees (−180 degrees) changes to draw an arc to be reduced. Since the operation force amount changes to drawn an arc, the endoscope 1 does not give a sense of awkwardness to operation by the user.

Further, in the endoscope, an operation force amount of an initial motion for turning the respective bending operation knobs 4 and 5 at the time when the bending section 12 is bent from the linear state (the neutral initial state) slightly increases from an operation force amount in the conventional general endoscope. However, since the operation force amount immediately decreases compared with the conventional endoscope, even a surgeon with less strength can comfortably and easily bend the bending section 12.

Therefore, the endoscope 1 is configured such that, when the bending section 12 is bend from the linear state, the operation force amounts of the respective bending operation knobs 4 and 5 immediately decrease from the initial motion and the bending section 12 can be easily bent with a light force.

According to the above explanation, in the endoscope in the present embodiment, after the bending operation knob at the time when the bending section 12 is bent from the linear state (the neutral initial state) is turned, the operation force amount immediately decreases. Therefore, even a surgeon with less strength can easily perform bending operation of the bending section 12.

Therefore, in the endoscope 1, when the bending section 12 is bent, the operation force amount of the bending operation knob from the linear state of the bending section 12 is reduced, the bending section 12 can be easily bent with a light force, and bending operability is improved.

Note that, in the endoscope 1 in the present embodiment, when the bending angle of the bending section 12 is set to 180 degrees (−180 degrees), turning amounts of the respective bending operation knobs 4 and 5 are set the same as the turning amounts of the general endoscope in which the bending angle is set to 180 degrees (−180 degrees). This is for clearly explanation in terms of calculation. In the endoscope 1, for example, when the bending angle of the bending section 12 is set to 180 degrees (−180 degrees), the turning amounts of the respective bending operation knobs 4 and 5 may be set to be smaller than the turning amounts in the general endoscope, that is, smaller than 180 degrees.

Second Embodiment

An endoscope in a second embodiment of the present invention is explained below with reference to the drawings.

Note that, in the following explanation, components same as the components described in the first embodiment are denoted by the same reference numerals and signs. Detailed explanation of the components is omitted.

Figure 10:
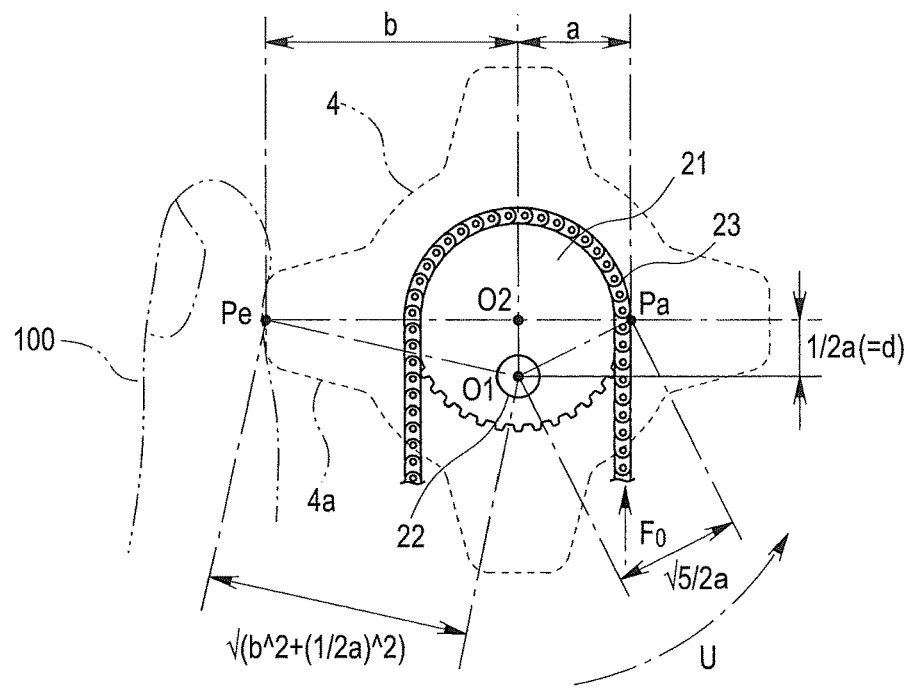
FIG. 10 is a schematic diagram showing a turning position of a bending operation knob at a time when a bending section is bent upward from an initial state in a second embodiment of the present invention.
Figure 11:
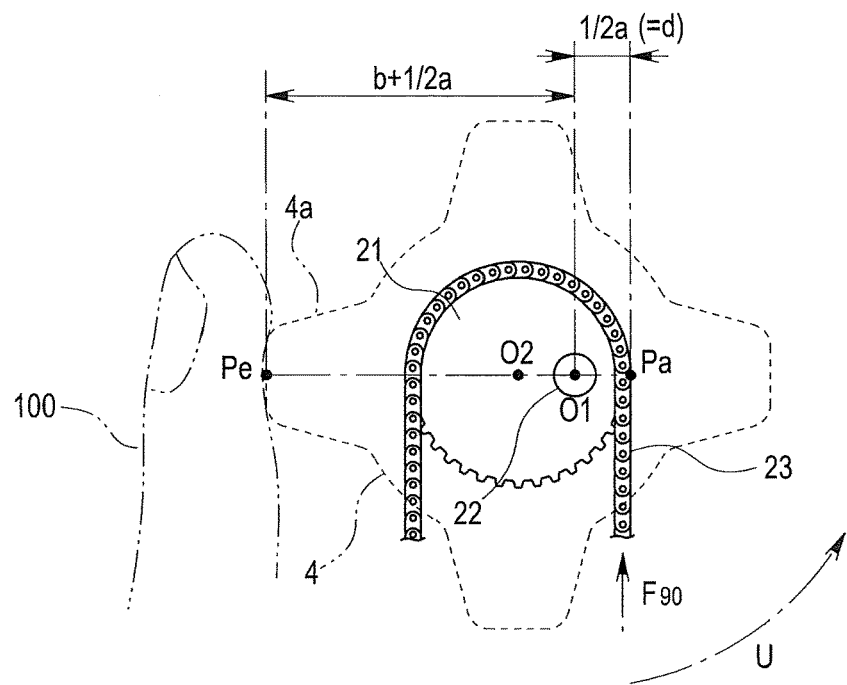
FIG. 11 is a schematic diagram showing a turning position of the bending operation knob at a time when the bending section is bent 90 degrees upward in the second embodiment of the present invention.
Figure 12:
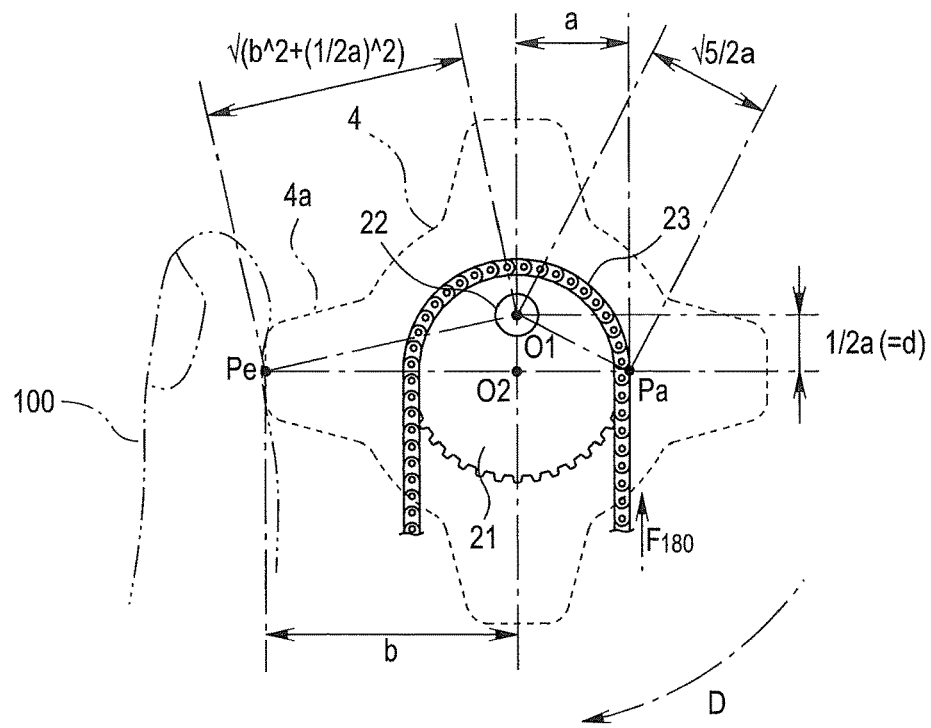
FIG. 12 is a schematic diagram showing a turning position of the bending operation knob at a time when the bending section is bent 180 degrees upward in the second embodiment of the present invention.
Figure 13:
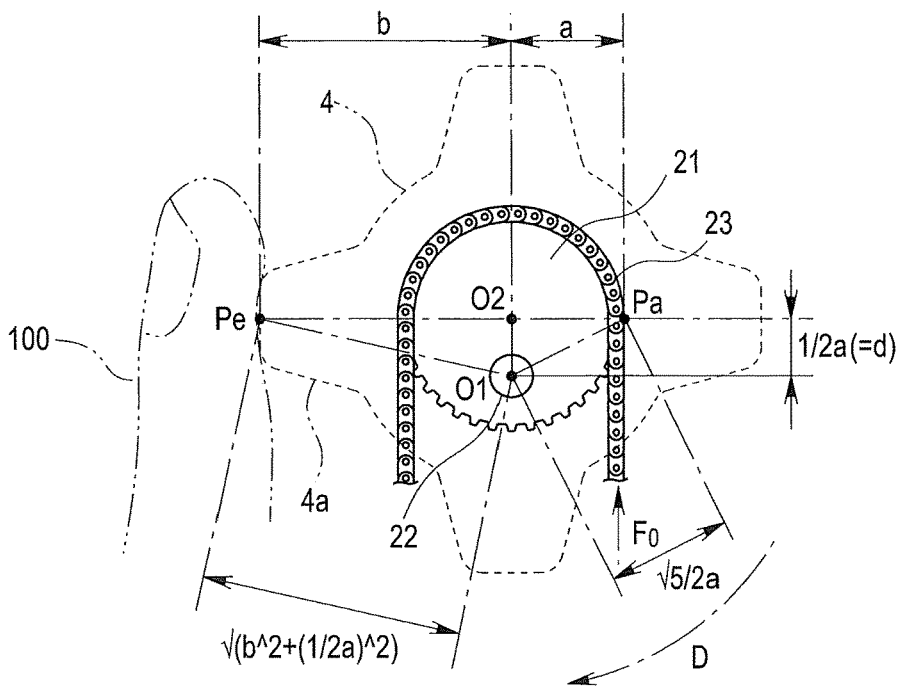
FIG. 13 is a schematic diagram showing a turning position of the bending operation knob at a time when the bending section is bent downward from the initial state in the second embodiment of the present invention.
Figure 14:
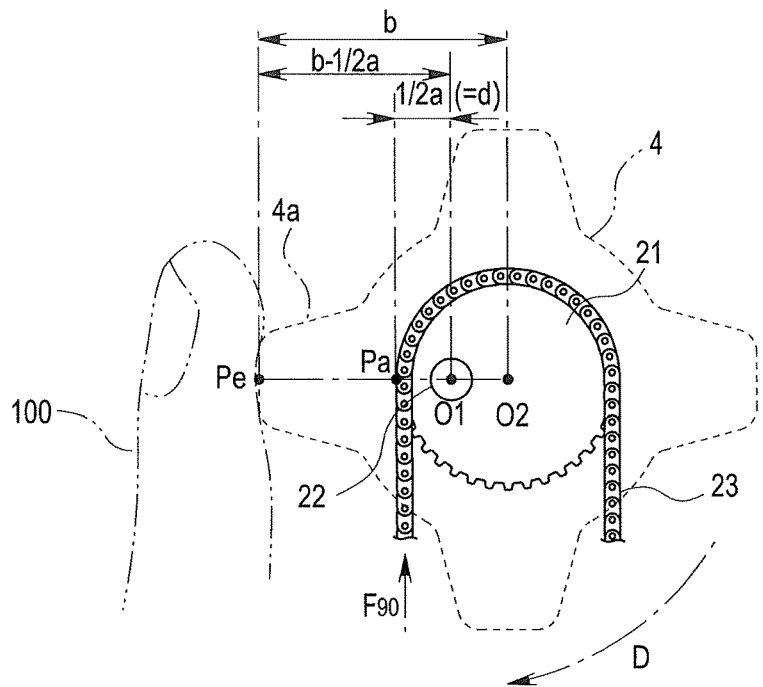
FIG. 14 is a schematic diagram showing a turning position of the bending operation knob at a time when the bending section is bent 90 degrees downward in the second embodiment of the present invention.
Figure 15:
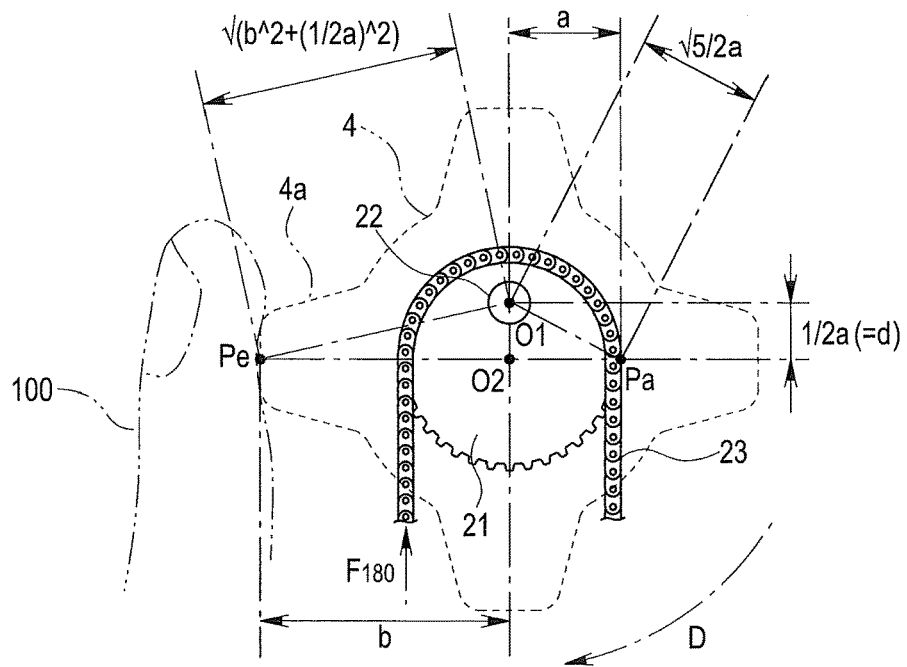
FIG. 15 is a schematic diagram showing a turning position of the bending operation knob at a time when the bending section is bent 180 degrees downward in the second embodiment of the present invention.
Figure 16:
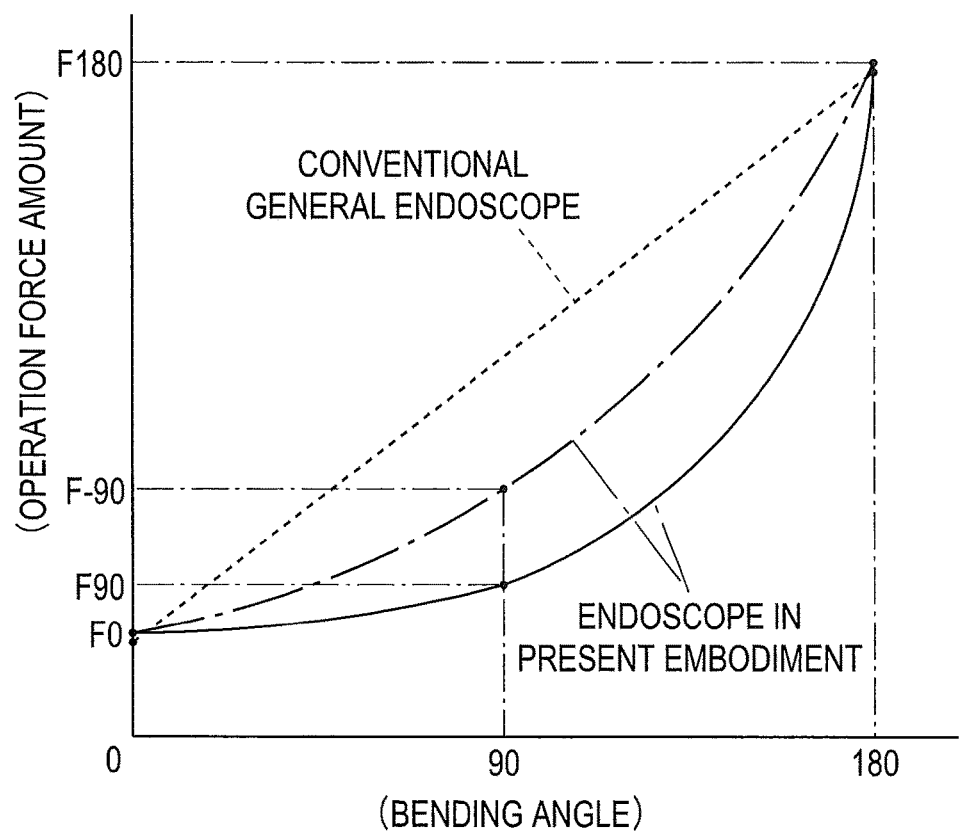
FIG. 16 is a graph showing a change in an operation force amount of the bending operation knob with respect to a bending angle of the bending section in the second embodiment of the present invention.
Figure 17:
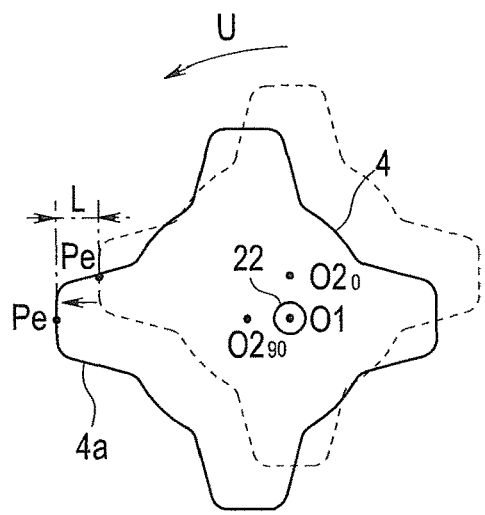
FIG. 17 is a schematic diagram for explaining a movement of the bending operation knob at a time when the bending section is bent 90 degrees upward from the initial state in the second embodiment of the present invention.
Figure 18:
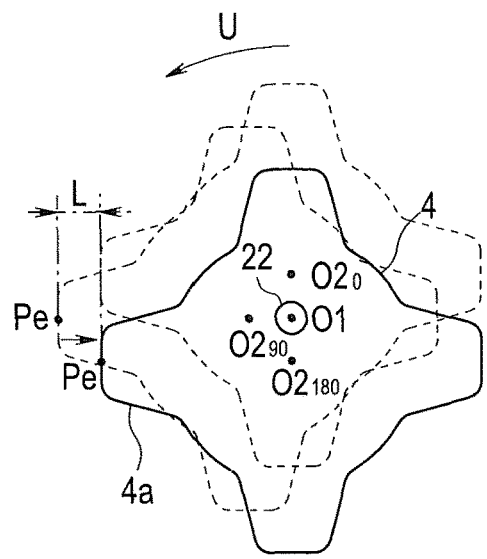
FIG. 18 is a schematic diagram for explaining a movement of the bending operation knob at a time when the bending section is bent 180 degrees upward from a 90 degree state in the second embodiment of the present invention.
Figure 19:
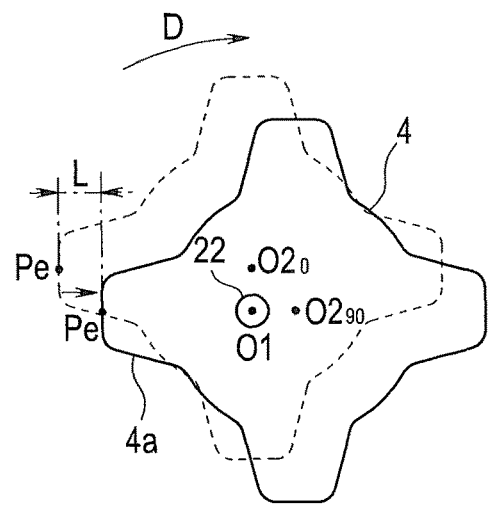
FIG. 19 is a schematic diagram for explaining a movement of the bending operation knob at a time when the bending section is bent 90 degrees downward from the initial state in the second embodiment of the present invention.
Figure 20:
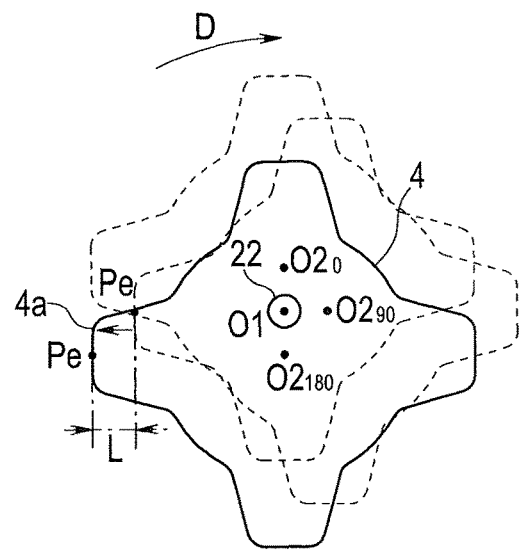
FIG. 20 is a schematic diagram for explaining a movement of the bending operation knob at a time when the bending section is bent 180 degrees downward from the 90 degree state in the second embodiment of the present invention.

FIG. 10 to FIG. 20 relate to the second embodiment of the present invention. FIG. 10 is a schematic diagram showing a turning position of a bending operation knob at a time when a bending section is bent upward from an initial state. FIG. 11 is a schematic diagram showing a turning position of the bending operation knob at a time when the bending section is bent 90 degrees upward. FIG. 12 is a schematic diagram showing a turning position of the bending operation knob at a time when the bending section is bent 180 degrees upward. FIG. 13 is a schematic diagram showing a turning position of the bending operation knob at a time when the bending section is bent downward from the initial state. FIG. 14 is a schematic diagram showing a turning position of the bending operation knob at a time when the bending section is bent 90 degrees downward. FIG. 15 is a schematic diagram showing a turning position of the bending operation knob at a time when the bending section is bent 180 degrees downward. FIG. 16 is a graph showing a change in an operation force amount of the bending operation knob with respect to a bending angle of the bending section. FIG. 17 is a schematic diagram for explaining a movement of the bending operation knob at a time when the bending section is bent 90 degrees upward from the initial state. FIG. 18 is a schematic diagram for explaining a movement of the bending operation knob at a time when the bending section is bent 180 degrees upward from a 90 degree state. FIG. 19 is a schematic diagram for explaining a movement of the bending operation knob at a time when the bending section is bent 90 degrees downward from the initial state. FIG. 20 is a schematic diagram for explaining a movement of the bending operation knob at a time when the bending section is bent 180 degrees downward from the 90 degree state.

In the endoscope 1 in the present embodiment, as shown in FIG. 10, the sprocket 21 and the respective bending operation knobs 4 and 5 are disposed such that centers (O2 in the figure) coincide with each other. Note that, in FIG. 10, only the up-down bending operation knob 4 is illustrated.

The up-down bending operation knob 4 (and the left-right bending operation knob 5) is a disk-like member in which four protrusion sections 4a for finger hook are radially provided from a center (a turning center). Note that, in the respective bending operation knobs 4 and 5, the number of protrusion sections 4a is not limited to four but may be five as in the first embodiment or may be any number equal to or more than two.

In the endoscope 1, the up-down bending operation knob 4 and the sprocket 21 are axially supported such that, when the bending section 12 is linear, the center O2 is decentered in a predetermined direction, in the figure, an upward side, which is a proximal end side, of the operation section 3 by the predetermined distance d from the turning center O1 of the turning shaft 22.

In other words, in the up-down bending operation knob 4 and the sprocket 21, the turning center O1 is decentered by the predetermined distance d to the distal end side along the longitudinal direction of the operation section 3 with respect to the center O2 of the up-down bending operation knob 4 and the sprocket 21.

Note that the center (the turning center) O1 of the turning shaft 22 and the center O2 of the sprocket 21 and the up-down bending operation knob 4 are juxtaposed along the center axis of the insertion section 2 when the bending section 12 is in the linear state (the neutral initial state).

Further, the same applies to the left-right bending operation knob 5. Explanation of components of the left-right bending operation knob 5 is omitted.

A relation between rotation angles and operation force amounts of the respective bending operation knobs 4 and 5 in the endoscope 1 configured as explained above is explained in detail below with reference to the drawings.

When the bending angle of the bending section 12 to be bent to an upward side is changed from 0 (zero) degrees in the initial state of the bending angle, in which the bending section 12 is linear, shown in FIG. 10 to 90 degrees, as shown in FIG. 11, the up-down bending operation knob 4 is turned 90 degrees around the turning center O1 in the counterclockwise direction.

In this state, an operation force amount necessary for the operation force amount $F_0$, which is a towing force of the operation wires 25 for bending the bending section 12 at a time when the bending section 12 is further bent to the upward side from the bending angle of 0 degrees, is the following Equation (10) from a relation between a distance $\sqrt{5}/2 \cdot a$ from the turning center O1 to the power point Pa and a distance $\sqrt{(b^2+(\frac{1}{2} \cdot a)^2)}$ from the turning center O1 to the action point Pe.

$$\text{Operation force amount } F0 = F_0 \cdot \sqrt{5}/2 \cdot a / \sqrt{(b^2+(\frac{1}{2} \cdot a)^2)} \quad (10)$$

Note that the distance from the turning center O1 to the power point Pa and the distance from the turning center O1 to the action point Pe can be calculated by a Pythagorean Theorem.

When the bending section 12 is further bent to the upward side from the state of the bending angle of 90 degrees shown in FIG. 11 to change the bending angle of the bending section 12 to 180 degrees, as shown in FIG. 12, the up-down bending operation knob 4 is turned 90 degrees around the turning center O1 in the counterclockwise direction. At this point, the up-down bending operation knob 4 and the sprocket 21 turn 90 degrees around the turning center O1 to approach the finger 100 of the user.

That is, when the bending angle of the bending section 12 is changed to 180 degrees to the upward side from the state of the bending angle of 0 (zero) degrees of the bending section 12 shown in FIG. 10, the up-down bending operation knob 4 is turned 180 degrees around the turning center O1 counterclockwise.

In this state, the operation force amount F90 necessary for the bending force amount $F_{90}$ for bending the bending section 12 at a time when the bending section 12 is further bent upward from the bending angle of 90 degrees is the following Equation (11) from a relation between the distance $\frac{1}{2} \cdot a$ from the turning center O1 to the power point Pa and a distance $b + \frac{1}{2} \cdot a$ from the turning center O1 to the action point Pe.

$$\text{Operation force amount } F90 = F_{90} \cdot 1/2 \cdot a / (b + 1/2 \cdot a) \quad (11)$$

Note that the operation force amount F180 necessary for the bending force amount $F_{180}$ at a time when the bending angle of the bending section 12 is changed to 180 degrees shown in FIG. 12 is the following Equation (12) from the relation between the distance $\sqrt{5}/2 \cdot a$ from the turning center O1 to the power point Pa and the distance $\sqrt{(b^2+(\frac{1}{2} \cdot a)^2)}$ from the turning center O1 to the action point Pe.

$$\text{Operation force amount } F180 = F_{180} \cdot \sqrt{5}/2 \cdot a / \sqrt{(b^2+(\frac{1}{2} \cdot a)^2)} \quad (12)$$

A relation between a rotation angle and an operation force amount of the up-down bending operation knob 4 at a time when the bending section 12 bends in a downward direction is explained below with reference to FIG. 13 to FIG. 15.

When the bending angle of the bending section 12 to be bent to a downward side is changed from 0 (zero) degrees in the initial state of the bending angle, in which the bending section 12 is linear, shown in FIG. 13 to 90 degrees (−90 degrees), as shown in FIG. 14, the up-down bending operation knob 4 is turned 90 degrees (−90 degrees) around the turning center O1 in the counterclockwise direction.

In this state, the operation force amount F0 necessary for the operation force amount $F_0$, which is a towing force of the operation wires 25 for bending the bending section 12 at a time when the bending section 12 is further bent to the downward side from the bending angle of 0 degrees, is the following Equation (13) from the relation between the distance $\sqrt{5}/2 \cdot a$ from the turning center O1 to the power point Pa and the distance $\sqrt{(b^2+(\frac{1}{2} \cdot a)^2)}$ from the turning center O1 to the action point Pe.

$$\text{Operation force amount } F0 = F_0 \cdot \sqrt{5}/2 \cdot a / \sqrt{(b^2+(\frac{1}{2} \cdot a)^2)} \quad (13)$$

When the bending section 12 is further bent to the downward side from the state of the bending angle of 90 degrees (−90 degrees) shown in FIG. 14 to change the bending angle of the bending section 12 to 180 degrees (−180 degrees), as shown in FIG. 15, the up-down bending operation knob 4 is further turned 90 degrees (−90 degrees) around the turning center O1 in the counterclockwise direction. At this point, the up-down bending operation knob 4 and the sprocket 21 turn 90 degrees (−90 degrees) around the turning center O1 to move away from the finger 100 of the user.

That is, when the bending angle of the bending section 12 is changed to 180 degrees (−180 degrees) to the downward side from the state of the bending angle of 0 (zero) degrees of the bending section 12 shown in FIG. 13, the up-down bending operation knob 4 is turned 180 degrees (−180 degrees) around the turning center O1 counterclockwise.

In this state, the operation force amount F90 (F-90) necessary for the bending force amount $F_{90}$ for bending the bending section 12 at a time when the bending section 12 is further bent downward from the bending angle of 90 degrees (−90 degrees) is the following Equation (14) from a relation between the distance $\frac{1}{2} \cdot a$ from the turning center O1 to the power point Pa and a distance $b - \frac{1}{2} \cdot a$ from the turning center O1 to the action point Pe.

$$\text{Operation force amount } F90 = F_{90} \cdot 1/2 \cdot a / (b - 1/2 \cdot a) \quad (14)$$

Note that the operation force amount F180 necessary for the bending force amount $F_{180}$ at a time when the bending angle of the bending section 12 is changed to 180 degrees (−180 degrees) shown in FIG. 15 is the following Equation (15) from the relation between the distance $\sqrt{5}/2 \cdot a$ from the turning center O1 to the power point Pa and the distance $\sqrt{(b^2+(\frac{1}{2} \cdot a)^2)}$ from the turning center O1 to the action point Pe.

$$\text{Operation force amount } F180 = F_{180} \cdot \sqrt{5}/2 \cdot a / \sqrt{(b^2+(\frac{1}{2} \cdot a)^2)} \quad (15)$$

On the other hand, in a general endoscope, as explained in the first embodiment, the relation between the distance a from the turning center O1 to the power point Pa and the distance b from the turning center O1 to the action point Pe is invariable.

Therefore, the operation force amount F0 necessary for the operation force amount $F_0$, which is a towing force of the operation wires 25 for bending the bending section 12 at a time when the bending section 12 is further bent to the upward/downward sides from the bending angle of 0 degrees, in the conventional endoscope is the following Equation (16) from the relation between the distance a from the turning center O1 to the power point Pa and the distance b from the turning center O1 to the action point Pe in both the upward and downward directions.

$$\text{Operation force amount } F0 = F_0 \cdot a / b \quad (16)$$

The operation force amount F90 necessary for the bending force amount $F_{90}$ for bending the bending section 12 at a time when the bending section 12 is further bent upward/downward from the bending angle of 90 degrees (−90 degrees) in the conventional endoscope is the following Equation (17) because the distance a from the turning center O1 to the power point Pa and the distance b from the turning center O1 to the action point Pe do not change in both the upward and downward directions.

$$\text{Operation force amount } F90 = F_{90} \cdot a/b \quad (17)$$

Further, the operation force amount F180 necessary for the bending force amount $F_{180}$ at a time when the bending angle of the bending section 12 is changed to 180 degrees (−180 degrees) in the conventional endoscope is the following Equation (18) because the distance a from the turning center O1 to the power point Pa and the distance b from the turning center O1 to the action point Pe do not change in both the upward and downward directions.

$$\text{Operation force amount } F180 = F_{180} \cdot a/b \quad (18)$$

A table summarizing the above is shown below.

TABLE 3

| | Bending angle of the bending section (Rotation angle of the bending operation knob) and operation force amount | | |
|---|---|---|---|
| | 0°/F0 | 90°/F90 | 180°/F180 |
| Decentering is absent (existing endoscope) | F0 · a/b | F90 · a/b | F180 · a/b |
| Decentering is present in an UP direction | $\dfrac{F_0 \cdot \sqrt{5}/2 \cdot a}{\sqrt{(b\char`\^2 + (1/2 \cdot a)\char`\^2)}}$ | $\dfrac{F_0 \cdot 1/2 \cdot a}{(b + 1/2 \cdot a)}$ | $\dfrac{F_0 \cdot \sqrt{5}/2 \cdot a}{\sqrt{(b\char`\^2 + (1/2 \cdot a)\char`\^2)}}$ |
| Decentering is present in a DOWN direction | $\dfrac{F_0 \cdot \sqrt{5}/2 \cdot a}{\sqrt{(b\char`\^2 + (1/2 \cdot a)\char`\^2)}}$ | $\dfrac{F_0 \cdot 1/2 \cdot a}{(b - 1/2 \cdot a)}$ | $\dfrac{F_0 \cdot \sqrt{5}/2 \cdot a}{\sqrt{(b\char`\^2 + (1/2 \cdot a)\char`\^2)}}$ |

In the endoscope 1, when the distance a from the turning center O1 to the power point Pa is a half (b=2a) of the distance b from the turning center O1 to the action point Pe, the respective equations (11) to (15) are calculated as follows.

$$F0 = F_0 \cdot \sqrt{5}/2 \cdot a/\sqrt{(b\char`\^2 + (½\cdot a)\char`\^2)} = F_0 \sqrt{5}/\sqrt{17} \quad (10),(13)$$

$$F90 = F_{90} \cdot 1/2 \cdot a/(2 \cdot a + 1/2 \cdot a) = F_{90} \cdot 1/5 \quad (11)$$

$$F90(F-90) = F_{90} \cdot 1/2 \cdot a/(2 \cdot a - 1/2 \cdot a) = F_{90} \cdot 1/3 \quad (14)$$

$$F180(F-180) = F_{180} \cdot \sqrt{5}/2 \cdot a/\sqrt{\{(2\cdot a)\char`\^2 + (½\cdot a)\char`\^2\}} = F_{180} \sqrt{5}/\sqrt{17} \quad (12),(15)$$

Note that, in the conventional endoscope, when the distance a from the turning center O1 to the power point Pa is a half (b=2a) of the distance b from the turning center O1 to the action point Pe, the respective equations (16) to (18) are calculated as follows.

$$F0 = F_0 \cdot a/2 \cdot a = F_0 \cdot 1/2 \quad (16)$$

$$F90 = F_{90} \cdot a/2 \cdot a = F_{90} \cdot 1/2 \quad (17)$$

$$F180 = F_{180} \cdot a/2 \cdot a = F_{180} \cdot 1/2 \quad (18)$$

A table summarizing the above is shown below.

TABLE 4

| | Bending angle of the bending section (Rotation angle of the bending operation knob) and operation force amount | | |
|---|---|---|---|
| | 0°/F0 | 90°/F90 | 180°/F180 |
| Decentering is absent (existing endoscope) | $F_0 \cdot 1/2$ | $F_{90} \cdot 1/2$ | $F_{180} \cdot 1/2$ |
| Decentering is present in an UP direction | $F_0 \cdot \sqrt{5}/\sqrt{17}$ | $F_{90} \cdot 1/5$ | $F_{180} \cdot \sqrt{5}/\sqrt{17}$ |
| Decentering is present in a DOWN direction | $F_0 \cdot \sqrt{5}/\sqrt{17}$ | $F_{90} \cdot 1/3$ | $F_{180} \cdot \sqrt{5}/\sqrt{17}$ |

The above is the explanation of the operation force amount of the up-down bending operation knob 4 with respect to the bending angle for bending the bending section 12. The same applies to the left-right bending operation knob 5. Therefore, explanation is omitted concerning the left-right bending operation knob 5.

In the endoscope 1 in the present embodiment, as shown in a graph of FIG. 16, when compared with a linear change indicated by a broken line in the figure due to an operation force amount of the conventional (existing) general endoscope, the operation force amount F0 in an initial motion from the bending angle of 0 degrees at a time when the bending section 12 is bent and the operation force amount F180 at the bending angle of 180 degrees (−180 degrees) are approximately 1.08 $\{=(F_0 \cdot \sqrt{5}/\sqrt{17})/(F_0 \cdot 1/2)=(F_{180} \cdot \sqrt{5})/(\sqrt{17}/F_{180} \cdot 1/2)\}$ times. The operation force amounts slightly increase.

However, in the endoscope 1, as indicated by a solid line in FIG. 16, the operation force amount F90 for bending the bending section 12 to the bending angle of 90 degrees upward is a force amount of $0.4\{=(F_{90} \cdot 1/5)/(F_{90} \cdot 1/2)\}$ times. As indicated by an alternate long and short dash line in FIG. 16, in the endoscope 1, the operation force amount F90 (F-90) for bending the bending section 12 downward to the bending angle of 90 degrees only has to be a force amount of approximately $0.67\{=(F_{90} \cdot 1/3)/(F_{90} \cdot 1/2)\}$ times. An operation force amount at the time when the bending section 12 is bent from the bending angle of 0 degrees to the bending angle of 180 degrees (−180 degrees) changes to draw an arc to be reduced.

As in the first embodiment, since the operation force amount changes to draw an arc, the endoscope 1 does not give a sense of awkwardness to operation by the user.

Therefore, as in the first embodiment, in the endoscope, an operation force amount of an initial motion for turning the respective bending operation knobs 4 and 5 at the time when the bending section 12 is bent from the linear state (the neutral initial state) slightly increases from an operation force amount in the conventional general endoscope. However, since the operation force amount immediately decreases compared with the conventional endoscope, even a surgeon with less strength can comfortably and easily bend the bending section 12.

Therefore, the endoscope 1 is configured such that, when the bending section 12 is bend from the linear state, the operation force amounts of the respective bending operation knobs 4 and 5 immediately decrease from the initial motion and the bending section 12 can be easily bent with a light force.

In the endoscope 1 in the present embodiment, in addition to the effects in the first embodiment, in particular, the operation force amount F90 for bending the frequently-used bending section 12 to the bending angle of 90 degrees upward is reduced to 0.4 times. It is possible to easily bend the bending section 12 with an extremely light force. The bending operability is further improved.

Note that, in the endoscope 1, in the up-down bending operation knob 4, the turning center O1 of the turning shaft 22 is decentered by the predetermined distance d to the distal end side along the longitudinal direction of the operation section 3 with respect to the center O2. Therefore, as shown in FIG. 17 and FIG. 18, during bending operation for bending the bending section 12 upward from the bending angle of 0 degrees to 180 degrees, the protrusion sections 4a of the up-down bending operation knob 4 turn around the turning center O1 to approach the finger 100 of the user at a predetermined distance L.

On the other hand, in the endoscope 1, as shown in FIG. 19 and FIG. 20, during bending operation for bending the bending section 12 downward from the bending angle of 0 degrees to 180 degrees, the protrusion sections 4a of the up-down bending operation knob 4 turn around the turning center O1 to move away from the finger 100 of the user at the predetermined distance L.

However, in the endoscope 1, as explained above, there are a lot of opportunities to bend the bending section 12 in the upward direction. In particular, for a surgeon having a small hand, there is an advantage that operation is easy when the protrusion sections 4a of the up bending operation knob 4 approach the finger 100.

The invention described in the respective embodiments explained above is not limited to the embodiments and the modifications and, besides, can be variously modified and implemented without departing from the spirit of the invention in an implementation stage. Further, the embodiments include inventions in various stages. Various inventions can be extracted by appropriate combinations in a disclosed plurality of constituent elements.

For example, when the described problems can be solved and the described effects can be obtained even if several constituent elements are deleted from all the constituent elements described in the embodiments, a configuration from which the constituent elements are deleted can be extracted as an invention.

What is claimed is:

1. An endoscope comprising:
    an operation section provided on a proximal end side;
    an insertion section extending to a distal end side from the operation section, a bending section being disposed in the insertion section;
    a towing member disposed in the insertion section and in the operation section from the bending section;
    a disk member turnably provided in the operation section and configured to turn to tow and loosen the towing member, the towing member comprising a wire extending from each of two sides of the disk member;
    an operation member disposed in the operation section such that a center of the operation member and a center of the disk member coincide with each other, the operation member being configured to turn the disk member to bend the bending section; and
    a turning shaft configured to turnably axially support the disk member and the operation member with respect to the operation section, the turning shaft being juxtaposed with the center of the disk member and the center of the operation member in a position decentered to the distal end side along a longitudinal direction of the operation section by a predetermined distance in an initial state in which the bending section is linear.

2. The endoscope according to claim 1, wherein, when the bending section is in the initial state, the center of the turning shaft and the center of the disk member and the operation member are juxtaposed along a center axis of the insertion section.

3. The endoscope according to claim 1, wherein
    the disk member is a chain wheel, and
    the towing member further comprises a chain that meshes with the chain wheel, where an end of each wire is connected to both ends of the chain.

* * * * *